United States Patent [19]

Luceri

[11] Patent Number: 4,623,340
[45] Date of Patent: Nov. 18, 1986

[54] ABSORBENT PRODUCT WITH COLOR CONTRASTED COVER PATTERN

[75] Inventor: Thomas J. Luceri, Little Ferry, N.J.

[73] Assignee: Personal Products Company, Milltown, N.J.

[21] Appl. No.: 532,890

[22] Filed: Sep. 16, 1983

[51] Int. Cl.⁴ .............................................. A61F 13/16
[52] U.S. Cl. .................... 604/385 R; 604/378; 604/370
[58] Field of Search ............... 604/378, 370, 380, 379, 604/385; 428/187, 207, 211, 198

[56] References Cited

U.S. PATENT DOCUMENTS 4,397,644 8/1983 Matthews et al. ............... 604/378
4,518,451 5/1985 Luceri et al. ..................... 604/378

Primary Examiner—Dalton L. Truluck
Assistant Examiner—Sherri E. Vinyard
Attorney, Agent, or Firm—Jason Lipow

[57] ABSTRACT

A cover is provided for a body fluid absorbing product which has a pattern of depressed and undepressed areas imposed on its exterior surface, which pattern presents a highly visible color contrast between the depressed and undepressed areas. The cover comprises a relatively light colored, relatively opaque outer cover having an interior layer of relatively dark color placed in face-to-face relationship with the interior surface of said outer cover and co-embossed.

24 Claims, 6 Drawing Figures

FIG-4
FIG-5
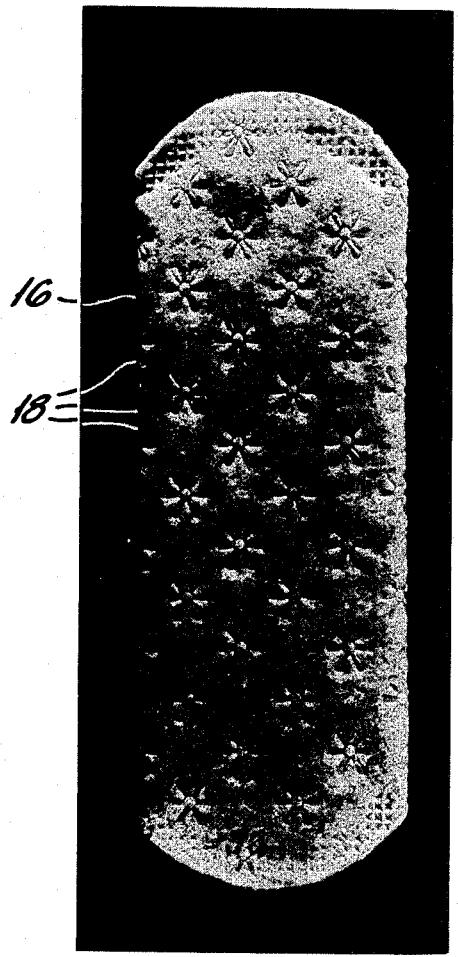
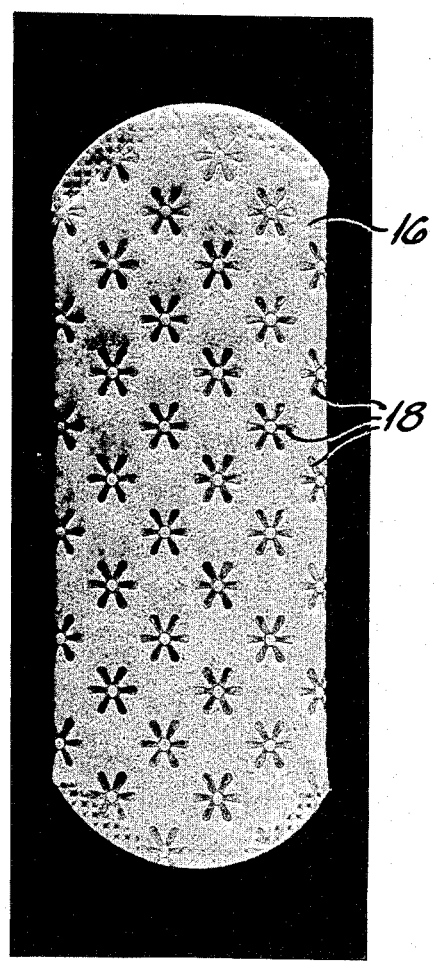

ABSORBENT PRODUCT WITH COLOR CONTRASTED COVER PATTERN

BACKGROUND OF THE INVENTION

This invention relates to products for absorbing body fluids such as for example disposable diapers, sanitary napkins, panty liners and the like. In particular, the invention relates to such products having an exterior surface which is provided with an aesthetically pleasing pattern.

Absorbent products having patterns imposed upon their exterior surfaces are now on the market. For example, sanitary napkins or the thinner version thereof, the so called panty liners, comprise a cover of nonwoven material having a pattern of depressed areas impressed into the external surface thereof in such configurations as flowers, lines, spots and the like. Needless to say, for such patterns to be aesthetically effective, the pattern must be visible to the eye. Such patterns owe their visability to the fact that, as a result of the compression step forming them, the depressed areas tend to be smoother and therefore reflect a greater amount of light as compared with the undepressed areas. Further, the variations in the topography, i.e., the juxtaposition of depressed and undepressed areas, produces shadows which highlight the pattern of depressions. Accordingly, it can be seen that pattern visability for products relying solely on depressed areas for creating such a pattern is a function of the degree of compression and the depth of the depressions. Said in other words, the greater the compression and the greater the depth of the depressions, the greater the visual contrast between depressed and undepressed areas. Unfortunately, these factors of compression and depth cannot always be increased to the point where sufficient contrast is manifested. Increasing the degree of compression in some instances will adversely effect the product from a functional point of view, e.g., render the product less receptive to absorbing and retaining body fluids or rendering the body contacting surface of the product uncomfortably stiff or harsh for the wearer. Similarly, the depth of the depressions is constrained in practice in that exterior covers for some of the products considered herein are inherently thin and thicker covers, as are also sometimes used, do not always take a permanent set without resorting to extreme compression conditions or without substantially modifying the manufacturing process for such products.

In commonly assigned, copending, patent application U.S. Ser. No. 414,104 now U.S. Pat. No. 4,518,451 filed on Sept. 9, 1982, there is described a product and method for producing a depressed pattern on an absorbent product without creating the functional disadvantage of harsh longitudinal edges. The product described therein has a deep pattern of depressions on the body facing surface and a shallow pattern of depressions on its longitudinal edges, this configuration being obtained by use of an insert of absorbent material being compressed together with portions of the cover and uncompressed at other cover portions. While this solution is effective for the products described in the aforementioned patent application, it is not applicable to several other product configurations wherein the aforementioned shortcomings of relying wholly on compression to provide pattern contrast apply.

Accordingly, there is a need for improvement in providing a product with a high degree of visual pattern contrast.

SUMMARY OF THE INVENTION

In accordance with the teachings of this invention a product for absorbing body fluids is provided with a pattern of depressed areas wherein the visual pattern contrast does not depend wholly upon the depth of the depressions or the degree of compression. Specifically, there is provided an improvement in a product for absorbing body fluids in which said product has an outer cover with an exterior and interior surface, and in which said cover has impressed therein a pattern of depressed areas. The outer cover of the improved product comprises a relatively light colored, relatively opaque sheet material comprising thermoplastic material. An interior layer is provided in face-to-face relationship with the interior surface of the outer cover, the interior layer being at least partially thermoplastic and relatively dark colored. It has been discovered that if the pattern of depressions is imposed upon the cover when the cover and the dark colored layer are in face-to-face relationship (i.e., coembossed), the depressed areas appear, as viewed from the external surface of the cover, as darker than the undepressed areas.

BRIEF DESCRIPTION OF THE DRAWINGS

FIG. 4 is a photograph illustrating a comparative product which does not incorporate the teachings of this invention;

FIG. 5 is a photograph of the product illustrated in FIG. 1; and

DETAILED DESCRIPTION OF THE INVENTION

Figure 1:
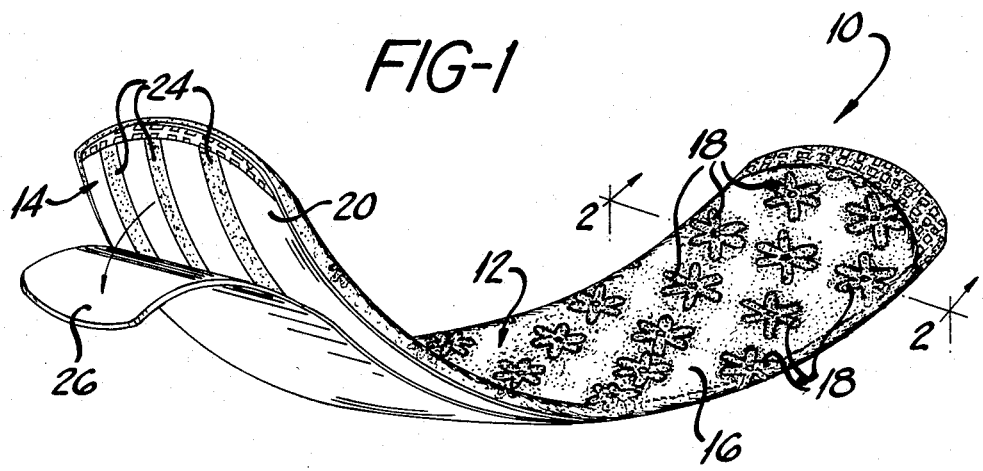
FIG. 1 is a perspective view of the absorbent product as a first embodiment of this invention, illustrated out of planar configuration to show both major surfaces and having its protective strip partially peeled from the garment side of the product.
Figure 2:
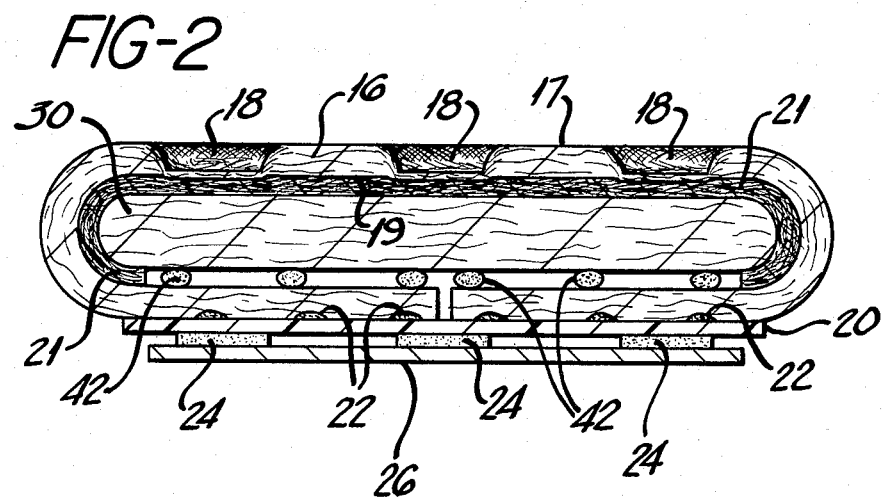
FIG. 2 is a transverse, cross-sectional view of the product of FIG. 1, taken through line 2—2 of FIG. 1.

The invention as broadly described above, is applicable to various kinds of absorbent products wherein it is desirable to obtain a visually contrasting pattern on one or more major surfaces. For example, the invention may be applicable to disposable diapers, full size sanitary napkins, panty shields, panty liners, bandages, incontinence pads and the like. For the purpose of illustration however, the following description, taken together with the drawings, shall be directed to the invention embodied in a thin panty liner which may be used both inter-and intra-menstrually. Referring now to FIGS. 1 and 2, illustrated therein, in perspective and transverse cross-sectional views, respectively is a panty liner 10 embodying the teachings of this invention. The liner 10 comprises a body facing, body fluid pervious side 12 and a garment facing, body fluid impervious side 14. The body facing side of the liner consists of a cover 16 having an exterior surface 17 and interior surface 19 and has impressed into its exterior surface 17, a pattern of depressed areas 18. As illustrated in FIG. 1, the pattern is in the form of a stylized snowflake design and is intended to add aesthetic value to the liner. It will be understood that any pattern may be freely substituted for the snowflake pattern illustrated in this specific embodiment and that the advantages of this invention, as herein set out and described, will equally pertain. For example, the pattern may take the form of various geometric shapes such as circles, diamonds, squares, curves or lines or other stylized figures such as flowers, stars, or the like.

Affixed to the garment facing side of the liner 10 is a layer of body fluid impervious material 20 provided to act as a barrier to body fluids and prevent the "strike through" of such fluids onto the undergarment of the wearer. This layer may comprise any thin flexible body fluid impermeable material such as, for example, a polymeric film, e.g., polyethylene, polypropylene, cellophane or even a normally fluid pervious material that has been treated to be impervious such as impregnated fluid repellant paper. As is illustrated in the drawings, the body fluid impervious layer 20 is affixed to the liner by means of a plurality of longitudinally extending lines of adhesive 22.

Disposed on the garment facing surface of the impervious layer 20 are longitudinally extending pressure-sensitive adhesive means 24, provided for attaching the liner to the crotch portion of an undergarment. While such adhesive means are illustrated in the form of longitudinally extending lines, it will be understood that various patterns such as spots, or transverse lines will be suitable. The adhesive employed may be any of the large number of pressure-sensitive adhesives available on the market, including for example, the water based pressure-sensitive sensitive adhesives such as the acrylate adhesives e.g., vinyl acetate-2 ethyl hexyl acetate copolymer which is generally combined with tackifiers such as ethylene amine. Alternatively, the adhesive may comprise the rapid-setting thermoplastic (hot melt) adhesives such as block copolymers exemplified by the A-B-A block copolymers wherein the A end block is polystyrene and the midblock is polyolefin copolymer such as poly (ethylene) poly(butylene)copolymer. The adhesive element may also comprise a double faced tape.

Overlying the adhesive elements 24 is a protective release strip 26 which is provided to protect the adhesive elements 24 from dirt and unintended adhesion prior to use. The strip 26 may be constructed of any suitable sheet-like material which adheres with sufficient tenacity to the adhesive element to remain in place prior to use but which can be readily removed when the liner is to be used. A particularly useful material is a semibleached kraft paper, the adhesive contacting side of which has been silicone treated to provide easy release from the adhesive elements 24.

In accordance with the teachings of this invention, the outer cover 16 comprises a nonwoven, relatively light colored, relatively opaque fabric comprising thermoplastic material. The cover may comprise any of the commonly utilized materials for the products considered herein and is selected to perform the traditional functions of such a cover i.e., to be comfortable when worn against the body, to allow body fluid to permeate into the body of the absorbent product and/or to aid in holding the product together in use. In this connection the cover may fully overwrap the product on all sides or may only partially overwrap the product, in particular on the body facing side. Thus, for example, the cover may be a thin sheet ranging in caliper from about 3 (0.0076 cm) to 10 mils (0.0254 cm) and having no substantial capacity for absorbing high volumes of body fluids. As such, such commonly used absorbent product cover materials may be used as, for example, woven or nonwoven fabrics consisting of fibers, filaments or the like including hydrophilic fibers such as cellulose, regenerated cellulose fiber or hydrophobic fibers as such synthetic fibers comprising polyolefins and the like or mixtures of the above. The cover may even comprise such usually fluid impermeable materials such as polymeric films which have been rendered fluid permeable by being provided with aperatures therein.

Alternatively, the cover may satisfy the traditional functions of a cover and, in addition, serve to absorb substantial volumes of body fluid. This latter embodiment is illustrated in the liner in FIGS. 1 and 2 wherein the cover 16 is chosen to be a material having some thickness, e.g., from about 10 mils (0.0254 cm) to about 200 mils (0.508 cm) and having absorptive capacity. As is illustrated in these figures, the cover 16 comprises a sheet of absorbent material folded about a centrally located planar insert 30 of absorbent material to further increase the absorptive capacity and thickness of the illustrated liner. As best viewed in FIG. 2, the cover is in a C-form configuration, enfolded about the insert 30 and held in place against the insert 30 by adhesive means 42.

The choice of materials for the absorbent cover and insert may vary widely provided, of course, that they conform to the above set out criteria. The materials recited in U.S. Pat. No. 4,023,571 issued May 17, 1977 to J. M. Comerford, et al. and in U.S. Pat. No. 4,023,570 issued on that same day to K. Chinai, et al. may be suitable. As described in these patents, a particularly useful material is the lofty and soft nonwoven, through bonded fabric described in U.S. Pat. No. 3,663,348 issued on May 16, 1972 to G. J. Liloia, et al. This fabric consists essentially of a mixture of approximately 25%, by weight, of long (about 2.9 cms.) rayon fibers and about 75% by weight of short (about 0.2 cm) wood pulp fibers and has a water dispersible binder applied throughout in an amount of between about 1% and about 30% of the weight of the fibers on a dry basis. The binders of choice are the self-curing acrylic latex type, the urethane type or other similar binders. The fabric has a weight of less than about 8 ounces per square yard and a density of about 0.15 to about 0.05 gm per cc.

Another particularly suitable absorbent material for use as both the absorbent sheet and the insert of this invention is a low density, highly absorbent, thermal bonded nonwoven fabric comprising a mixture of absorbent fibers and staple length polyester/polyethylene conjugate fibers. The absorbent fibers are preferably wood pulp or other cellulosic fibers which may have been treated to enhance absorbency. The conjugate fibers are fibers which comprise a polyester core surrounded by a sheath of polyethylene.

Preferably, the conjugate fibers employ high density polyethylene, that is, linear polyethylene that has a density of at least 0.94, and a Melt Index (as determined by ASTMD-1238E ettod, employing the parameters of 190° C. and 2160 gm) of greater than 1, preferably greater than about 10, and more preferably from about 20 to about 50. The fibers may comprise from about 40 to 60 percent, by weight polyester and preferably from 45 to 55 weight percent polyester, the remainder being polyethylene. Such fibers may be used in deniers of from 1 to about 6 and may be from about ½ inch to about 3 or 4 inches long. Preferably the fabric comprise outer layers of heat fusible fibers having the mixture of wood pulp and conjugate fibers sandwiched therebetween. Such outer layers may consist of the conjugate fibers or may in fact be any heat-fusible materials such as polypropylene fibers, for example. The fabric is stabilized by applying heat thereto under essentially zero pressure whereby thermal bonding takes place without destroying the integrity of the fibers and low density is maintained. Typically, the bulk density of such fabrics is less than about 0.15 grams per cubic centimeter.

As prescribed herein and best viewed in FIG. 2, an interior layer 21 is provided in face-to-face relationship with the interior surface 19 of the cover 16. Such interior layer is relatively dark colored and preferably comprises thermoplastic material. It will be understood that as used herein the terms "relatively dark" and "relatively light" as used in connection with the interior layer and the outer cover elements, respectively, mean the degree of color contrast of these elements relative to each other.

The essential feature of this invention is that these elements i.e., the outer cover and the interior layer, are provided as co-embossed. By the term "co-embossed" it is meant that the pattern of depressed areas 18 are provided on the outer surface 17 of the cover 16 when the interior layer is in face-to-face relationship with the interior surface 19 of the cover 16. Thus, for example, such co-embossing may be accomplished by first positioning said cover and interior layer in such face-to-face relationship, then imposing the pattern of depressed areas, and then assembling the final product. Alternatively, the product may be wholly or partially assembled with the cover and interior layer in its final position and then the co-embossing or the imposing of the pattern of depressed areas may be effected. It is also possible that the cover and interior layer may be placed into the prescribed relationship and co-embossed while the product is in an intermediate stage of manufacture. For example, such co-embossing may take place when the cover, interior layer and the insert 30 are assembled, but before the body fluid impervious layer 20 is applied or before the cover is folded to envelop the insert 30. This latter application of this invention would then be amenable to incorporation of the teachings of the aforementioned U.S. patent application Ser. No. 414,104.

As is illustrated in FIG. 2, the relatively dark fluid pervious, thermoplastic interior layer 21 may be in the form of a sheet or web of colored material such as film or fiber which sheet has mechanical integrity by itself and which is then placed into the prescribed position with the cover for co-embossing. The sheet may obtain such integrity by adhesive binders, heat bonds, hydrogen bonds or simply by mechanical entanglement in the case of a long fibered interior sheet.

Figure 3:
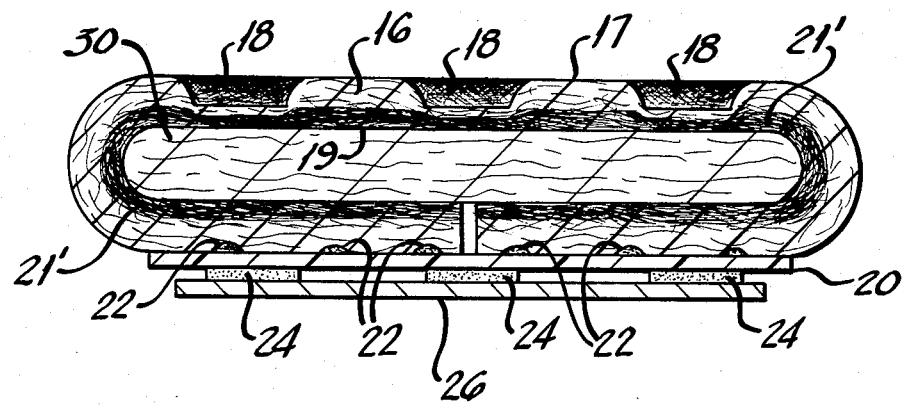
FIG. 3 is a transverse, cross-sectional view of a product similar to that of FIG. 1 as a second embodiment of this invention.

FIG. 3 illustrates an alternative embodiment of this invention wherein the interior layer 21' is not a separate, self-sustaining sheet but instead is integral with the cover 16. In this alternative embodiment the interior layer 21' comprises fibers having a relatively dark pigmentation which are bonded to the interior surface 19 of the cover 16 to form the interior layer. Such bonding may be accomplished by adhesives, heat bonds, or the like. It may also be possible to simply position a layer of unbonded, dark colored fibers in face-to-face relationship with the interior surface of the cover prior to co-embossing.

A particularly suitable method of providing the interior layer 21' is applicable when employing the above mentioned thermal bonded non-woven fabric as the cover material. In this circumstance the cover comprises outer layers of heat fusible fibers having a mixture of wood pulp and conjugate fibers sandwiched therebetween. The layer of fusile fibers which is applied to the interior surface of the cover may then be comprised of pigmented fibers and, as such, may constitute the relatively dark interior layer of this invention.

Referring now to FIG. 5, illustrated therein is a photograph of a panty liner made in accordance with the teachings of this invention and having the construction illustrated in FIGS. 1 and 2. The cover 16, in this depicted product is the thermal bonded fabric described above, having a basis weight of 1.5 ounces per square yard and comprising, overall 35%, by weight, of wood pulp fibers and 65% be weight, of conjugate fibers having a polyester core and a high density polyethylene sheath. The conjugate fibers have a staple length of 3.8 cm. and a denier of 3.0. The materials are so distributed as to provide a pulp/conjugate fiber mixture sandwiched between two veneers of conjugate fibers, the veneers having a basis weight of 0.37 ounces per square yard, and 0.32 ounces per square yard, with heavier veneer ultimately being employed on the exterior surface of the cover. The fabric is stabilized by passing hot air through the fibers and thereby melting the high density polyethylene which bonds the fibers together upon cooling. The fabric has a thickness of about 0.07 cm, a machine and cross direction tensile strength of 5.8 and 1.0 pounds/inch of width, respectively, and is capable of holding about 20 times its own weight of distilled water.

The interior layer 21 used in this product is a blue pigmented non-woven melt blown polypropylene fabric manufactured by the Riegel Division of James River Corporation of Milford, N.J., U.S.A. The fabric fibers are pigmented during the fiber extrusion process by mixing the polypropylene resin with a pigmented resin. The fabric is formed by processes described in U.S. Pat. Nos. 3,595,245; 3,704,198; and 3,825,380 and has a basis weight of 0.59 ounces per square yard, a thickness of 0.0079 inches, a tensile strength of 1.32 lbs./in. and an elongation to break of 45.6%.

The interior layer and the cover are co-embossed by placing the interior layer into face-to-face relationship with the interior surface of the cover and impressing the snowflake pattern of depression 18 into the exterior surface of the cover. As can be seen by examination of FIG. 5, the depressed areas 18 provide great visual contrast with the undepressed portion of the cover.

Figure 6:
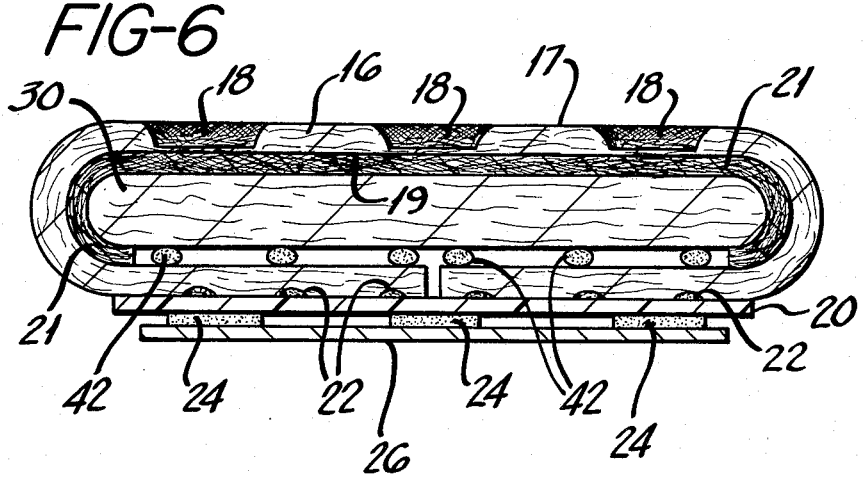
FIG. 6 is a transverse, cross-sectional view of the comparative product shown in FIG. 4.

As a comparison, FIG. 4 is a photograph of a panty liner which does not utilize the teachings of this invention. The construction of the panty liner of FIG. 4 is illustrated; in transverse cross-sectional view in FIG. 6 and is identical to that of FIG. 5 with respect to materials of construction and their relative positioning, with the exception that the cover and the interior layer for this comparative product are not co-embossed. Instead, the pattern of depressed areas 18 are first imposed into the exterior surface of the cover and then the cover is placed into face-to-face relationship with the interior layer. Said in other words, the cover and interior layer are not co-embossed.

As a result, and in clear contradistinction from the panty liner of FIG. 4, the panty liner of FIG. 5 offers poor visual contrast between the depressed areas 18 and the undepressed area.

What is claimed is:

1. In a product for absorbing body fluids comprising:
an outer cover having an exterior and interior surface comprising thermoplastic material;
an interior layer in face-to-face relationship with the interior surface of said outer cover;
said outer cover and said interior layer being co-embossed to impose a pattern of depressed areas and undepressed areas into the exterior surface of said outer cover;
the improvement wherein:
said outer cover is light colored and said interior layer is dark colored, relative to each other, and said undepressed areas of said cover are opaque relative to said depressed areas whereby said depressed areas color contrast with said undepressed areas.

2. The product of claim 1 wherein said interior layer is a separate self-substaining sheet prior to co-embossing.

3. The product of claim 2 wherein said interior layer is a heat bonded web of thermoplastic fibers, said fibers having a dark pigmentation.

4. The product of claim 1 wherein said interior layer comprises a layer of dark pigmented fibers bonded to said interior surface of said cover prior to co-embossing.

5. The product of claim 4 wherein said exterior surface of said cover comprises non-pigmented heat fusible fibers, said interior surface of said cover comprises a mixture of wood pulp fibers and conjugate fibers, and said interior layer comprises pigmented heat fusible fibers.

6. The product of claim 1 wherein said interior layer comprises unbonded pigmented fibers prior to co-embossing.

7. The product of claim 1 as a sanitary napkin.

8. The product of claim 1 as a panty liner.

9. The product of claim 1 as a disposable diaper.

10. In a method for manufacturing an outer cover for a product for absorbing body fluids said product comprising an outer cover and an interior layer wherein said outer cover has an interior and exterior surface and the interior surface of said outer cover is positioned in face-to-face relationship with said interior layer and co-embossed to impose a pattern of depressed and undepressed areas into the exterior surface of said outer cover, the improvement comprising:
selecting an outer cover having a relatively light color and an interior layer having a relatively dark color, said colors being relative to each other;
said outer cover being relatively opaque, in its unembossed state, relative to the observation of the dark colored interior layer therethrough;
whereby, when said cover and interior layers are co-embossed, said depressed areas color contrast with said undepressed areas.

11. In a sanitary napkin comprising:
an outer cover having an exterior and interior surface comprising thermoplastic material;
an interior layer in face-to-face relationship with the interior surface of said outer cover;
said outer cover and said interior layer being co-embossed to impose a pattern of depressed areas and undepressed areas into the exterior surface of said outer cover;
the improvement wherein:
said outer cover is light colored and said interior layer is dark colored, relative to each other, and said undepressed areas of said cover are opaque relative to said depressed areas whereby said depressed areas color contrast with said undepressed areas.

12. The sanitary napkin of claim 11 wherein said interior layer is a separate self-sustaining sheet prior to co-embossing.

13. The sanitary napkin of claim 12 wherein said interior layer is a heat bonded web of thermoplastic fibers, said fibers having a dark pigmentation.

14. The sanitary napkin of claim 11 wherein said interior layer comprises a layer of dark pigmented fibers bonded to said interior surface of said cover prior to co-embossing.

15. The sanitary napkin of claim 14 wherein said exterior surface of said cover comprises non-pigmented heat fusible fibers, said interior surface of said cover comprises a mixture of wood pulp fibers and conjugate fibers, and said interior layer comprises pigmented heat fusible fibers.

16. The sanitary napkin of claim 11 wherein said interior layer comprises unbonded pigmented fibers prior to co-embossing.

17. In a method for manufacturing an outer cover for a sanitary napkin said napkin comprising an outer cover and an interior layer wherein said outer cover has an interior and exterior surface and the interior surface of said outer cover is positioned in face-to-face relationship with interior layer and co-embossed to impose a pattern of depressed and undepressed areas into the exterior surface of said outer cover, the improvement comprising:
selecting an outer cover having a relatively light color and an interior layer having a relatively dark color, said colors being relative to each other;
said outer cover being relatively opaque, in its unembossed state, relative to the observation of the dark colored interior layer therethrough;
whereby, when said cover and interior layers are co-embossed, said depressed areas color contrast with said undepressed areas.

18. In a disposable diaper comprising:
an outer cover having an exterior and interior surface comprising thermoplastic material;
an interior layer in face-to-face relationship with the interior surface of said outer cover;
said outer cover and said interior layer being co-embossed to impose a pattern of depressed areas and undepressed areas into the exterior surface of said outer cover;
the improvement wherein:
said outer cover is light colored and said interior layer is dark colored, relative to each other, and said undepressed areas of said cover are opaque relative to said depressed areas whereby said depressed areas color contrast with said undepressed areas.

19. The disposable diaper of claim 18 wherein said interior layer is a separate self-sustaining sheet prior to co-embossing.

20. The disposable diaper of claim 19 wherein said interior layer is a heat bonded web of thermoplastic fibers, said fibers having a dark pigmentation.

21. The disposable diaper of claim 18 wherein said interior layer comprises a layer of dark pigmented fibers bonded to said interior surface of said cover prior to co-embossing.

22. The disposable diaper of claim 21 wherein said exterior surface of said cover comprises non-pigmented heat fusible fibers, said interior surface of said cover comprises a mixture of wood pulp fibers and conjugate fibers, and said interior layer comprises pigmented heat fusible fibers.

23. The disposable diaper of claim 18 wherein said interior layer comprises unbonded pigmented fibers prior to co-embossing.

24. In a method for manufacturing an outer cover for a disposable diaper said diaper comprising an outer cover and an interior layer wherein said outer cover has an interior and exterior surface and the interior surface of said outer cover is positioned in face-to-face relationship with said interior layer and co-embossed to impose a pattern of depressed and undepressed areas into the exterior surface of said outer cover, the improvement comprising:
- selecting an outer cover having a relatively light color and an interior layer having a relatively dark color, said colors being relative to each other;
- said outer cover being relatively opaque, in its unembossed state, relative to the observation of the dark colored interior layer therethrough;
- whereby, when said cover and interior layers are co-embossed, said depressed areas color contrast with said undepressed areas.

* * * * *